US006486300B1

(12) United States Patent
Bandman et al.

(10) Patent No.: US 6,486,300 B1
(45) Date of Patent: *Nov. 26, 2002

(54) HUMAN NM23-LIKE PROTEIN

(75) Inventors: Olga Bandman; Phillip R. Hawkins, both of Mountain View, CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/460,532

(22) Filed: Dec. 13, 1999

Related U.S. Application Data

(62) Division of application No. 09/199,842, filed on Nov. 24, 1998, now Pat. No. 6,087,125, which is a division of application No. 08/713,825, filed on Sep. 13, 1996, now Pat. No. 5,874,285.

(51) Int. Cl.[7] .......................... C07K 17/00; C12K 1/00; G01N 33/53; C12Q 1/48
(52) U.S. Cl. ............................ 530/350; 435/4; 435/7.1; 435/15
(58) Field of Search .............................. 530/350; 435/4, 435/7.1, 15

(56) References Cited

FOREIGN PATENT DOCUMENTS

WO          9105793      * 5/1991

OTHER PUBLICATIONS

Alberts et al (Molecular BIology of the Cell, 3rd Ed., 1994, Garland Publishing, Inc., New York, p. 465).*
Shantz and Pegg (Int. J. Biochem. Cell Biol., 1999, 31:107–122.*
McClean and Hill (Eur. J. Cancer, 1993, 29A:2243–2248).*
Fu et al (EMBO J., 1996, 15:4392–4401).*
Bowie et al (Science, 1990, 257:1306–1310).*
Burgess et al (J of Cell Bio., 111:2129–2138, 1990).*
Lazar et al (Mol Cell Bio., 1988, 8:1247–1252).*
Reiger et al (Glossary of Genetics and Cytogenetics, Classical and Molecular, 4th Ed., Springer–Verlag, Berlin, 1976, p. 17).*
Weber et al (Int. J. Biochem. Cell Biol., 27:215–224, 1995).*
Lasko, M., et al., "Embryonic Expression of nm23 during Mouse Organogenesis" *Cell Growth & Differ.,* 3:873–879 (1992).
Leone, A., et al., "Reduced Tumor Incidence, Metastatic Potential, and Cytokine Responsiveness of nm23–Transfected Melanoma Cells" *Cell,* 65:25–35 (1991).
Baba, H. et al., "Two Isotypes of Murine nm23/Nucleoside Diphosphate Kinase, nm2–M1 and nm23–M2, Are Involved in Metastatic Suppression of a Murine Melanoma Line" *Cancer Res.,* 55:1977–1981 (1995).

Rosengard, A.M., et al., "Reduced nm23/Awd protein in tumour metastasis and aberrant *Drosophila* development" *Nature,* 342:177–180 (1989).
Gilles, A.M., et al., "Nucleoside Diphosphate Kinase from Human Erythrocytes", *J. Biol. Chem.,* 266:8784–8789 (1991).
Postel, E.H., et al., "Human c–myc Transcription Factor PuF Identified as nm23–H2 Nucleoside Diphosphate Kinase, a Candidate Suppressor of Tumor Metastasis", *Science,* 261:478–480 (1993).
Postel, E.H., et al., "Nucleoside Diphosphate Kinase Enzyme Activity of NM23–H2/PuF Is Not Required for Its DNA Binding and in Vitro Transcriptional Functions", *J. Biol. Chem.,* 269:8627–8630 (1994).
MacDonald, N.J., et al., "A Serine Phosphorylation of Nm23, and Not Its Nucleoside Diphosphate Kinase Activity, Correlates with Suppression of Tumor Metastatic Potential", *J. Biol. Chem.,* 268:25780–25789 (1993).
Lakshmi, M.S. et al., "Metastasis Associated MTS1 and NM23 Genes Affect Tubulin Polymerisation in B16 Melanoma: A Possible Mechanism of Their Regulation of Metastatic Behaviour of Tumours" *Anticancer Res.* 13:299–303 (1993).
Venturelli, D., et al., "Overexpression of DR–nm23, a protein encoded by a member of the nm23 gene family, inhibits ganulocyte differentiation and induces apoptosis in 32Dc13 myeloid cells" *Proc. Natl. Acad. Sci.,* 92:7435–7439 (1995).
Hennessy, C., et al., "Expression of the Antimetastatic Gene nm23 in Human Breast Cancer: An Association With Good Prognosis" *J. Natl. Cancer Inst.* 83:281–285 (1991).
Stahl, J.A., et al., "Identification of a Second Human nm23 Gene, nm23–H2" *Cancer Res.,* 51:445–449 (1991).
Tokunaga, Y., et al., "Reduced Expression of nm23–H1, But Not of nm23–H2, is Concordant with the Frequency of Lymph–Node Metastasis of Human Breast Cancer" *Int. J. Cancer,* 55:66–17 (1993).
Steeg, P.S., et al., "Nm23 and breast cancer metastasis" *Breast Cancer Res. & Treat.,* 25:175–187 (1993).

(List continued on next page.)

*Primary Examiner*—Susan Ungar
(74) *Attorney, Agent, or Firm*—Incyte Genomics, Inc.

(57) ABSTRACT

The present invention provides polynucleotides which identify and encode a novel human nm23-like protein (H-nm23). The invention provides for genetically engineered expression vectors and host cells comprising the nucleic acid sequence encoding H-nm23 and for a method for producing the protein. The invention also provides for the use of substantially purified H-nm23 for the for the treatment of diseases associated with the expression of H-nm23. The invention also describes diagnostic assays which utilize diagnostic compositions comprising the polynucleotides which hybridize with naturally occurring sequences encoding H-nm23 and antibodies which specifically bind to the protein.

8 Claims, 8 Drawing Sheets

OTHER PUBLICATIONS

Howlett, A.R., et al., "A Novel Function for the nm23–H1 Gene: Overexpression in Human Breast Carcinoma Cells Leads to the Formation of Basement Membrane and Growth Arrest" *J. Natl. Cancer Inst.,* 86:1838–1844 (1994).

Kapitanovic, S. et al., "nm23–H1 Gene Expression in Ovarian Tumors—A Potential Tumor Marker" *Anticancer Res.,* 15:587–590 (1995).

Viel, A., et al., "Suppressive Role of the Metastasis–related nm23–H1 Gene in Human Ovarian Carcinomas: Association of High Messenger RNA Expression with Lack of Lymph Node Metastasis" *Cancer Res.,* 55:2645–2650 (1995).

Florenes, V.A. et al., "Levels of nm23 Messenger RNA in Metastatic Malignant Melanomas: Inverse Correlation to Disease Progression" *Cancer Res.,* 52:6088–6091 (1992).

Xerri, L., et al., "NM23 expression in metastasis of malignant melanoma is a predictive prognostic parameter correlated with survival" *Br. J. Cancer,* 70:1224–1228 (1994).

Iizuka, N., et al., "NM23–H1 and NM23–H2 Messenger RNA Abundance in Human Hepatocellular Carcinoma" *Cancer Res.,* 55:652–657 (1995).

Fishman, J.R., et al., "Quantitation of NM23 Expression in Human Prostate Tissues" *J. Urol.,* 152:202–207 (1994).

Yamashiro, S., et al., "Alteration of nm23 gene expression during the induced differentiation of human leukemia cell lines" *Oncogene,* 9:2461–2468 (1994).

Zou, M., et al., "High levels of Nm,23 gene expression in advanced stage of thyroid carcinomas" *Br. J. Cancer,* 68:385–388 (1993).

Yamaguchi, A., et al., "Inverse association of nm23–H1 expression by colorectal cancer with liver metastasis" *Br. J. Cancer,* 68:1020–1024 (1993).

Zeng, Z.S., et al., "High level of Nm23–H1 gene expression is associated with local colorectal cancer progression not with metastases" *Br. J. Cancer,* 70:1025–1030 (1994).

Hailat, N. et al., "High Levels of p19/nm23 Protein in Neuroblastoma Are Associated with Advanced Stage Disease and with N–myc Gene Amplification" *J. Clin. Invest.,* 88:341–345 (1991).

Engel, M. et al., "High Levels of NM23–H1 and NM23–H2 Messenger RNA in Human Squamous–Cell Lung Carcinoma are Associated with Poor Differentiation and Advanced Tumor Stages" *Int. J. Cancer* 55:375–379 (1993).

Kanayama, H. et al., "Analysis of nm32 Gene Expressions in Human Bladder and Renal Cancers" *Int. J. Urol.,* 1:324–331 (1994).

Dooley, S., et al., "Isolation and characterization of the human genomic locus coding for the putative metastasis control gene nm23–H1" *Human Genet.,* 93:63–66 (1994).

Webb, P.A., "The Crystal Structure of a Human Necleoside Diphosphate Kinase, NM23–H2" *J. Mol. Biol.,* 251:574–587 (1995).

Database Swissprot, Acc. No. P27950, Aug. 1, 1992, Kasahara, M., et al., "Nucleoside Diphosphate Kinase," XP002054675.

Database GenBank, Genbank Acc. No. G06857, CA Reg. No. 166793–42–6, 19 Oct. 1995, Hudson, T., "Whitehead Institute/MIT Center for Genome Research; Physically Mapped ESTs", XP002054676.

Database GenBank, Genbank Acc. No. R53008, CA Reg. No. 165843–22–1, May 18, 1995, Hillier, L., et al., "The WashU–Merck EST Project," XP002054677.

Burgess, W.H. et al., "Possible Dissociation of the Heparin-binding and Mitogenic Activities of Heparin–binding (Acidic Fibroblast) Growth Factor–1 from Its Receptor–binding Activities by Site–directed Mutagenesis of a Single Lysine Residue", *J. Cell Biol.,* 111:2129–2138 (1990).

Tao, M.H. and S.L Morrison, "Studies of Aglycosylated Chimeric Mouse–Human IgG: Role of Carbohydrate in the Structure and Effector Functions Mediated by the Human IgG Constant Region", *J. Immunol.,* 143: 2595–2601 (1989).

Lazar, E. et al., "Transforming Growth Factor α: Mutation of Aspartic Acid 47 and Leucine 48 Results in Different Biological Activities", *Mol. and Cell. Bio.,* 8: 1247–1252 (1988).

Hemmerich, S. et al., "A Cromoglycate Binding Protein from Rat Mast Cells of Leukemia Line Is a Nucleoside Diphosphate Kinase", *Biochemistry,* 31: 4574–4579 (1992).

Milon, L. et al., (GI 1945761), GenBank Sequence Database (Accession Y07604), National Center for Biotechnology Information, National Library of Medicine, Bethesda, Maryland 20894 (Apr. 22, 1997).

Milon, L. et al. (GI 1945762), GenBank Sequence Database (Accession CAA68877), National Center for Biotechnology Information, National Library of Medicine, Bethesda, Maryland 20894 (Apr. 22, 1997).

Milon, L. et al., "nm23–H4, a new member of the family of human nm23/nucleoside diphosphate kinase genes localised on chromosome 1613," *Hum. Genet* (1997) 99:550–557.

EMBL Entry Acc. No.: Y07604 (Apr. 22, 1997).

* cited by examiner

FIGURE 1A

```
                       9              18             27             36             45             54
5' GG  CCG  GGC  GTC  ATG  GGC  GGC  CTC  TTC  TGG  CGC  TCC  GCG  CTG  CGG  GGG  CTG  CGC
                       M    G    G    L    F    W    R    S    A    L    R    G    L    R 63                          72             81             90             99            108
   TGC  GGC  CCG  CGG  GCC  CCG  GGC  CCG  AGC  CTG  CTA  GTG  CGC  CAC  GGC  TCG  GGA  GGG
    C    G    P    R    A    P    G    P    S    L    L    V    R    H    G    S    G    G 117                         126            135            144            153            162
   CCC  TCC  TGG  ACC  CGG  GAG  CGG  ACC  CTG  GTG  GCG  GTG  AAG  CCC  GAT  GGC  GTG  CAA
    P    S    W    T    R    E    R    T    L    V    A    V    K    P    D    G    V    Q 171                         180            189            198            207            216
   CGG  CGG  CTC  GTT  GGG  GAC  GTG  ATC  CAG  CGC  TTT  GAG  AGG  CGG  TTC  ACG  CTG
    R    R    L    V    G    D    V    I    Q    R    F    E    R    R    F    T    L 225                         234            243            252            261            270
   GTG  GGG  ATG  AAG  ATG  CTG  CAA  GCA  CCA  GAG  AGC  GTC  CTT  GCC  GAG  CAC  TAC  CAG
    V    G    M    K    M    L    Q    A    P    E    S    V    L    A    E    H    Y    Q 279                         288            297            306            315            324
   GAC  CTG  CGG  AGG  AAG  CCC  TTC  TAC  CCT  GCC  CTM  ATC  CGC  TAC  ATG  AGC  TCT  GGG
    D    L    R    R    K    P    F    Y    P    A    L    I    R    Y    M    S    S    G 333                         342            351            360            369            378
   CCT  GTG  GTG  GCC  ATG  GTC  TGG  GAA  GGG  TAC  AAT  GTC  CGC  GCC  TCR  AGG  GCC
    P    V    V    A    M    V    W    E    G    Y    N    V    R    A    S    R    A
```

```
      387             396             405             414             423             432
ATG ATT GGA CAC ACC GAC TCG GCT GAG GCT GCC CCA GGA ACC ATA AGG GGT GAC
 M   I   G   H   T   D   S   A   E   A   A   P   G   T   I   R   G   D 441             450             459             468             477             486
TTC AGC GTC CAC ATC AGC AGG AAT GTC ATC CAC GCC AGC GAC TCC GTG GAG GGG
 F   S   V   H   I   S   R   N   V   I   H   A   S   D   S   V   E   G 495             504             513             522             531             540
GCC CAG CGG GAG ATC CAG CTG TGG TTC CAG AGC AGT GAG CTG GTG AGC TGG GCA
 A   Q   R   E   I   Q   L   W   F   Q   S   S   E   L   V   S   W   A 549             558             567             576             585             594
GAC GGG GGC CAG CAC AGC AGC ATC CAC CAC CCA GCC TGA GGC TCA AGC TGC CCT TAC
 D   G   G   Q   H   S   S   I   H   H   P   A   *

603             612             621             630             639             648
CAC CCC ATC CCC CAC GCA GGA CCA ACT ACC TCC GTC AGC AAG AAC CCA AGC CCA 657             666             675             684             693             702
CAT CCA AAC CTG CCT GTC CCA AAC CAC TTA CTT CCC TGT TCA CCT CTG CCC CAC 711             720             729             738             747             756
CCC AGC CCA GAG GAG TTT GAG CCA ACT TCA GTG CCT TTC TGT ACC CCA AGC
```

FIGURE 1B

```
      765         774         783     792         801         810
CAG CAC AAG ATT GGA CCA ATC CTT TTT GCA CCA AAG TGC CGG ACA ACC TTT GTG 819         828         837     846         855         864
GTG GGG GGT CTT CAC ATT ATC ATA ACC TCT CCT CTA AAG GGG AGG CAT TAA 873         882         891     900         909         918
AAT TCA CTG TGC CCA GCA CAT GGG TGG TAC ACT AAT TAT GAC TTC CCC CAG CTC 927         936         945     954         963         972
TGA GGT AGA AAT GAC GCC TTT ATG CAA GTT GTA AGG AGT TGA ACA GTA AAG AGG

981
AAG TTT TGC ACA CCC 3'
```

FIGURE 1C

```
  1  MGGLFWRSALRGLRCGPRAPGPSLLVRHGS                    In 964996
  1  M----------------------------ICLVLTIFANLFPAACT    GI 1051255 DR-nm23
  1  M-----------------------------------------         GI 468542 nm23 H1
  1  M-----------------------------------------         GI 127983 nm23 H2

31  GGPSWTRERTLVAVKPDGVQRRLVGDVIQR                    In 964996
 19  GA------HERTFLAVKPDGVQRRLVGEIVRR                  GI 1051255 DR-nm23
  2  AN------CERTFIAIKPDGVQRGLVGEIHKR                  GI 468542 nm23 H1
  2  AN------LERTFIAHKPDGVQRGLVGEIHKR                  GI 127983 nm23 H2

61  FERRGFTLVGMKMLQAPESVLAEHYQDLRR                    In 964996
 45  FERKGFKLVALKLVQSEELLREHYAELRE                     GI 1051255 DR-nm23
 28  FEQKGFRLVGLKFMQASEDLLKEHYVDLKD                    GI 468542 nm23 H1
 28  FEQKGFRLVAMKFLRASEEHLKQHYIDLKD                    GI 127983 nm23 H2

91  KPFYPALIRYMSSGPVVAMWEGYNVVRAS                     In 964996
 75  RPFYGRLVKYMASGPVVAMVWQGLDVVRTS                    GI 1051255 DR-nm23
 58  RPFFAGLVKYMHSGPVVAMWEGLNVVKTG                     GI 468542 nm23 H1
 58  RPFPGLVKYMNSGPVVAMWEGLNVVKTG                      GI 127983 nm23 H2

121  RAMIGHTDSAEAAPGTIRGDFSVHISRNVI                    In 964996
105  RALIGATNPADAPPGTIRGDFCIEVG-NLH                    GI 1051255 DR-nm23
 88  RVMLGETNPADSKPGTIRGDFCIQVGRNIH                    GI 468542 nm23 H1
 88  RVMLGETNPADSKPGTIRGDFCIQVGRNIH                    GI 127983 nm23 H2
```

| Library | Lib Description | Abun | Pct Abun |
|---|---|---|---|
| DUODNOT02 | small intestine, duodenum, 8 F | 3 | 0.0787 |
| PROSNOT14 | prostate, 60 M, match to PROSTUT08 | 3 | 0.0767 |
| HNT3AZT01 | hNT2 cell line, teratocarcinoma, treated AZ | 1 | 0.0685 |
| OVARNOT02 | ovary, 59 F | 2 | 0.0630 |
| FIBRSEM01 | fibroblasts, senescent, NORM, WM | 2 | 0.0624 |
| LNODNOT03 | lymph node, 67 M | 2 | 0.0530 |
| PROSNOT16 | prostate, 68 M | 3 | 0.0500 |
| CARDFEM01 | heart, fetal, NORM, WM | 1 | 0.0473 |
| SCORNOT01 | spinal cord, 71 M | 2 | 0.0402 |
| LNODNOT02 | lymph nodes, 42 F | 1 | 0.0335 |
| SPLNFEM01 | spleen, fetal, WM | 1 | 0.0332 |
| BRSTNOT02 | breast, 55 F, match to BRSTTUT01 | 2 | 0.0317 |
| THYRNOT02 | thyroid, hyperthyroidism, 16 F | 1 | 0.0303 |
| BRSTTUT01 | breast tumor, 55 F, match to BRSTNOT02 | 2 | 0.0302 |
| LUNGFEM01 | lung, fetal, NORM, WM | 2 | 0.0296 |
| DUODNOT01 | small intestine, duodenum, 41 F | 1 | 0.0287 |
| PROSNOT11 | prostate, 28 M | 1 | 0.0282 |
| PROSTUT12 | prostate tumor, 65 M, match to PROSNOT20 | 3 | 0.0279 |
| BLADNOT04 | bladder, 28 M | 1 | 0.0278 |
| BRAITUT12 | brain tumor, astrocytoma, 40 F, match to BRAINOT14 | 1 | 0.0272 |
| PROSTUT10 | prostate tumor, 66 M, match to PROSNOT15 | 1 | 0.0268 |
| KIDNNOT09 | kidney, fetal M | 1 | 0.0267 |

FIGURE 4A

| | | |
|---|---|---|
| PROSTUT08 | prostate tumor, 60 M, match to PROSNOT14 | 1 | 0.0266 |
| PROSTUT09 | prostate tumor, 66 M | 1 | 0.0264 |
| LUNGNOT10 | lung, fetal M | 1 | 0.0261 |
| LIVRTUT01 | liver tumor, metastasis, 51 F | 1 | 0.0259 |
| PROSNOT18 | prostate, 58 M | 1 | 0.0256 |
| BLADTUT04 | bladder tumor, 60 M, match to BLADNOT05 | 2 | 0.0253 |
| PROSNOT15 | prostate, 66 M, match to PROSTUT10 | 1 | 0.0241 |
| COLNTUT02 | colon tumor, 75 M, match to COLNNOT01 | 1 | 0.0220 |
| CRBLNOT01 | brain, cerebellum, 69 M | 1 | 0.0195 |
| LUNGFET03 | lung, fetal F | 2 | 0.0183 |
| SINTBST01 | small intestine, ileum, Crohn's, 18 F | 1 | 0.0168 |
| KIDNNOT05 | kidney, neonatal F | 1 | 0.0161 |
| BRSTNOT05 | breast, 58 F, match to BRSTTUT03 | 1 | 0.0154 |
| LATRTUT02 | heart tumor, myoma, 43 M | 1 | 0.0137 |
| UCMCL5T01 | mononuclear cells, treated IL-5 | 1 | 0.0125 |
| PROSTUT04 | prostate tumor, 57 M, match to PROSNOT06 | 1 | 0.0117 |
| MELANOM01 | melanocytes, M, NORM, WM | 1 | 0.0096 |
| LIVSFEM02 | liver/spleen, fetal M, NORM, WM | 1 | 0.0080 |
| PLACNOM02 | placenta, neonatal F, NORM, WM | 1 | 0.0056 |

FIGURE 4B

HUMAN NM23-LIKE PROTEIN

This application is a divisional application of U.S. application Ser. No. 09/199,842, filed Nov. 24, 1998, now U.S. Pat. No. 6,087,125 which is a divisional application of U.S. application Ser. No. 08/713,825, filed Sep. 13, 1996, issued Feb. 23, 1999, as U.S. Pat. No. 5,874,285.

FIELD OF THE INVENTION

The present invention relates to nucleic acid and amino acid sequences of a novel human nm23-like protein and to the use of these sequences in the diagnosis, study, prevention and treatment of disease.

BACKGROUND OF THE INVENTION

The nm23 genes encode proteins that participate in the development and differentiation of normal tissues. Nm23 proteins are also associated with the regulation of tumor metastasis. Homologs of the highly conserved protein have been characterized in numerous tissues including those from humans, mice, Drosophila, and Myxococcus xanthus. The nm23 proteins generally consist of 150 to 180 amino acid residues. All known nm23 proteins contain a leucine zipper motif and exhibit nucleoside diphosphate kinase (NDPK) activity.

Nm23 protein accumulation is coincident with the functional differentiation of multiple epithelial tissues in the developing mouse. At the onset of organogenesis, the amount of nm23 protein is relatively low and uniform throughout the mouse embryo. The protein begins to accumulate preferentially in the first embryonic tissues to differentiate, the developing nervous system and heart. Subsequent differentiation of liver, kidney, skin, intestine, adrenal, and stomach epithelial cells is accompanied by increased nm23 protein expression (Lasko M et al (1992) Cell Growth Differ 3:873–879).

In rodent, reduced expression of the nm23 gene systems has been correlated with increased potential for tumor metastasis. A suppressive effect of nm23 on several aspects of the cancer process, including metastasis, has been demonstrated in murine melanoma cells (Leone A et al (1991) Cell 65: 25–35). The number of metastases developed in a murine melanoma subline was inversely correlated with the expression of two murine isotypes, nm23-M1 and nm23-M2 (Baba H et al (1995) Cancer Res 55:1977–1981).

In Drosophila, an nm23 homologue, abnormal wing discs (awd), is essential for normal development. Mutation or reduced expression of awd causes abnormal tissue morphology, necrosis and widespread aberrant differentiation similar to malignant progression (Rosengard A M et al (1989) Nature 342:177–180).

Two human nm23 isoforms, nm23-H1 and nm23-H2, each consist of 152 amino acid residues with Mr of 17,143 and 17,294, respectively. The isoforms have 88% sequence identity and encode polypeptides identical to the A and B chains of human erythrocyte NDPK (Gilles et al (1991) J Biol Chem 266:8784–8789). NDPK is a hexameric enzyme, with isozymes consisting of all combinations of the A and B chains (A6, A5B . . . AB5, B6). NDPK transfers a phosphoryl group between nucleoside tri- and diphosphates via a covalent phosphoenzyme intermediate. In nm23-H1 and H2, histidine 118 is the site of this transient phosphorylation.

Human nm23-H2 protein is also identical.to the c-myc purine-binding transcription factor PuF (Postel EH et al (1993) Science 261:478–480). Myc, the protein product of the c-myc proto-oncogene, is a proposed to modulate the expression of genes involved in cellular proliferation, differentiation, and tumor formation. Native PuF and purified recombinant nm23-H2 bind to DNA sequences corresponding to a nuclease-hypersensitive element (NHE) in the human c-myc P1 promoter, and induce accurate c-myc transcription in vitro.

The relationship between the DNA binding, transcriptional activation, and NDPK activities of nm23 was assessed by site-directed mutagenesis of recombinant nm23-H2. Although the NDPK phosphoenzyme active site mutant H118F was inactive in NDPK assays, it displayed normal DNA binding affinity for the c-myc promoter and retained full c-myc transcriptional activity in vitro (Postel E H and Ferrone C A (1994) J Biol Chem 269:8627–8630). This suggests that the DNA binding/transcriptional activation and the NDPK activities of nm23-H2 are independent properties of the nm23 proteins which may be associated with different biological functions.

The mechanism by which nm23 affect metastasis and development is unclear. Autophosphorylation of serine has been observed in nm23, distinct from NDPK-associated histidine phosphorylation (MacDonald N J et al (1993) J Biol Chem 268:25780–25789). A direct correlation has been observed in mice between in vivo nm23 serine phosphorylation levels and suppression of tumor metastatic potential among control and nm23-M1 transfected murine melanoma cells. The serine phosphorylation of mouse nm23 is inhibited by cAMP in vitro and forskolin in vivo, suggesting that this phosphorylation is regulated by a signal transduction pathway. No correlation was found between nm23 NDPK activity and melanoma cell metastasis, nor was NDPK activity inhibited by cAMP (MacDonald, supra).

Co-regulated expression of nm23 and mts1 (cyclin-dependent protein kinase), another tumor-suppressor gene, alters the state of tubulin polymerization in B16 melanoma cell lines (Lakshmi M S et al (1993) Anticancer Res 13:299–303). The altered tubulin polymerization is suggested to impart invasive and metastasizing properties to the cell line.

Recently, a new human nm23 isoform, DR-nm23, has been cloned from a chronic myelogenous leukemia (CML) blast crisis cell line (Venturelli D et al (1995) Proc Natl Acad Sci USA 92:7435–7439). The DR-nm23 protein consists of 168 amino acids, and has 67% and 69% sequence identity to the nm23-H1 and H2 isoforms, respectively. DR-nm23 is involved in normal hematopoiesis and, when overexpressed, may contribute to differentiation arrest, a feature of blastic transformation in CML.

The NM23 Gene Family and Cancer

Expression levels of nm23 have been monitored throughout the development and metastasis of several types of cancer. In some tumors types, an inverse correlation exists between expression of nm23 and metastasis. For instance, elevated nm23 expression in human breast cancer tumors is associated with a decrease in lymph node metastasis and with longer patient survival. The nm23 gene product may play an important role in suppressing the metastatic phenotype (Hennessy et al (1991) J Natl Cancer Inst 83: 281–285). Stahl et al ((1991) Cancer Res 51:445–449) report that metastatic breast tumors exhibit significantly reduced levels of the nm23-H1 protein relative to the nm23-H2 protein. Tokunaga Y et al ((1993) Int J Cancer 55:66–71) likewise report that expression of nm23-H1, but not nm23-H2, is inversely associated with lymph-node metastasis. Overall survival is better in patients in which nm23-H1 expression is elevated than in those in which it is lowered. Nm23-H1 therefore has value for predicting long-term survival of human breast-cancer patients.

Steeg P S et al ((1993) Breast Cancer Res Treat 25:175–187) report a significant association between reduced nm23 expression, at the RNA or protein levels, and aggressive tumor growth in human breast cancer. Decreases in nm23 expression begin prior to actual histologically identifiable invasion. Expression of human nm23-H1 cDNA in the transfected metastatic human MDA-MB-435 breast carcinoma cell line suppresses metastatic potential by 50–90%. Transfection of human breast carcinoma cell lines with a nm23-H1 expression vector restores many phenotypically normal features to these cells (Howlett A R et al (1994) J Natl Cancer Inst 86: 1838–1844).

Differences in expression levels of nm23-H1 have been reported among normal ovary tissue, benign tumors and carcinomas. The nm23-H1 protein is absent from metastatic ovarian carcinomas more often than non-metastatic carcinomas (Kapitanovic S et al (1995) Anticancer Res 15:587–590). Tumors that do not metastasize into the lymph nodes express nm23-H1 at significantly higher levels than tumors that do metastasize into the lymph nodes. These observations suggest that the nm23-H1 protein may have an inhibitory effect on lymphatic metastasis (Viel A et al (1995) Cancer Res 55:2645–2650).

Low levels of nm23 mRNA also correlate with high metastatic potential in malignant melanomas (Florenes V A et al (1992) Cancer Res 52: 6088–91). However, patients with higher nm23 expression in metastatic tissue tend to live longer (Xerri L et al (1994) Br J Cancer 70:1224–1228).

Similar correlations between nm23 and metastasis are reported for hepatocellular carcinomas (Iizuka et al. 95), prostate cancer (Fishman et al. 94), and leukemia cell lines (Yamashiro et al. 94).

However, among other tumor types, nm23 expression has no apparent relationship to metastatic potential. Expression of nm23 even correlates directly with severity in some of these cancers. For instance, nm23 expression in various types of thyroid cancers does not appear to play a role in metastasis. The average level of nm23 gene expression in stages I through III of differentiated thyroid carcinoma is comparable to that in multinodular goiters. In advanced stages of thyroid carcinoma (stage IV and anaplastic), a 2-fold increase in nm23 expression is observed. This suggests a direct correlation of nm23 expression with rapid cell proliferation in thyroid cancer (Zou M et al (1993) Br J Cancer 68:385–388).

Yamaguchi A et al ((1993) Br J Cancer 68:1020–1024) report that no significant correlation exists between nm23-H1 expression and colorectal tumor histology, serosal invasion, lymphatic invasion, venous invasion, or lymph node metastasis. However, Zeng Z S et al ((1994) Br J Cancer 70:1025–1030) report that nm23-H1 expression increases with local colorectal tumor severity, and in liver metastases even higher levels of nm23-H1 expression are found. In addition, Zeng et al (supra) observed two immunoreactive species of nm23-H1 expressed in roughly equal proportions in 16 patients: the predicted 17 kDa form and a larger 18.5 kDa form.

High expression levels of a 19 kDa form of nm23-H1 protein in neuroblastoma are associated with advanced stage (III and IV) disease and with N-myc gene amplification (Hailat N et al (1991) J Clin Invest 88: 341–345).

Engel M et al ((1993) Int J Cancer 55:375–9) show that high levels of nm23-H1 and nm23-H2 mRNA in human squamous-cell lung carcinoma, large-cell carcinoma, sarcoma, and carcinoids are associated with poor differentiation, advanced stage tumors and poor prognosis. In human renal carcinoma cell lines and in high stage renal cancers, levels of nm23-H1 and nm23-H2 mRNAs were elevated (Kanayama H et al (1994) Int J Urol 1: 324–331).

The discovery of DR-nm23 (Venturelli D et al, supra) raises the possibility that additional nm23-like proteins present in human tissues mediate normal or abnormal cellular processes within those tissues. Along with its diagnostic and therapeutic value, the nm23 proteins have a pronounced prognostic value for those types of tumors in which a relationship between expression of nm23 and metastasis exist. Nm23 is also useful in diagnostic, prognostic and therapeutic applications for those tumor types for which levels of expression correlate with tumor severity. Therefore, the selective modulation of the expression or activity of a novel nm23-like protein may allow the successful treatment of amenable types of cancer.

SUMMARY OF THE INVENTION

The present invention discloses a novel nm23-like protein, hereinafter referred to as H-nm23, having chemical and structural homology to human nm23 isoforms DR-nm23, nm23-H1 and nm23-H2. Accordingly, the invention features a substantially purified H-nm23, encoded by amino acid sequence of SEQ ID NO:1, having structural characteristics of the family of nm23 proteins.

One aspect of the invention features isolated and substantially purified polynucleotides which encode H-nm23. In a particular aspect, the polynucleotide is the nucleotide sequence of SEQ ID NO:2. In addition, the invention features nucleotide sequences which hybridize under stringent conditions to SEQ ID NO:2.

The invention further relates to nucleic acid sequence encoding H-nm23, oligonucleotides, peptide nucleic acids (PNA), fragments, portions or antisense molecules thereof. The present invention also relates to an expression vector which includes polynucleotide encoding H-nm23 and its use to transform host cells or organisms. The invention also relates to antibodies which bind specifically to the nm23 having amino acid sequence of SEQ ID NO:1 and to a pharmaceutical composition comprising a substantially purified nm23 having amino acid sequence of SEQ ID NO:1.

BRIEF DESCRIPTION OF THE FIGURES

FIGS. 1A, 1B and 1C show the amino acid sequence (SEQ ID NO:1) and the nucleic acid sequence (SEQ ID NO:2) of the human nm23-like protein H-nm23. The alignment was produced using MACDNASIS software (Hitachi Software Engineering Co Ltd, San Bruno Calif.).

FIGS. 2A and 2B shows the amino acid sequence alignments among H-nm23 (SEQ ID NO:1), the human nm23 isoforms DR-nm23 (GI 1051256; SEQ ID NO:3), nm23-H1 (GI 468542; SEQ ID NO:4), and nm23-H2 (GI 127983, SEQ ID NO:5). The multisequence alignment program of DNASTAR software (DNAStar Inc, Madison Wis.) was used.

FIGS. 4A and 4B list Incyte libraries in which full-length or partial H-nm23 mRNA sequences are represented, the abundance of the sequences, and the percent abundance.

DETAILED DESCRIPTION OF THE INVENTION

Definitions

Figure 3:
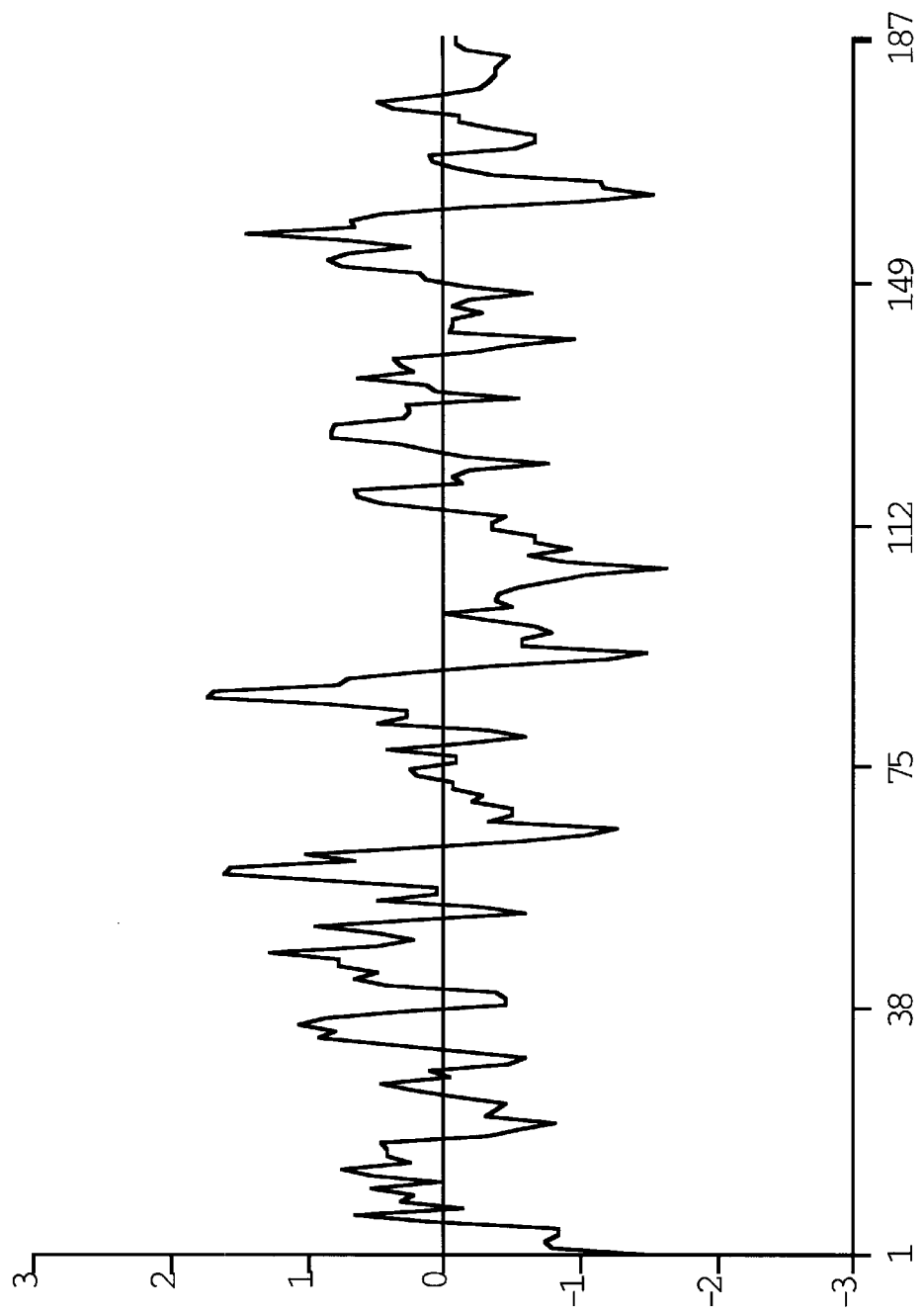
FIG. 3 shows the hydrophobicity plot (generated using MACDNASiS software) for H-nm23, SEQ ID NO:1; the X axis reflects amino acid position, and the negative Y axis, hydrophobicity.

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amino acid sequence as used herein refers to peptide or protein sequence. "Consensus" as used herein may refer to a nucleic acid sequence 1) which has been resequenced to resolve uncalled bases, 2) which has been extended using XL-PCR (Perkin Elmer) in the 5' or the 3' direction and resequenced, 3) which has been assembled from the overlapping sequences of more than one Incyte clone GCG Fragment Assembly System, (GCG, Madison Wis.), or 4) which has been both extended and assembled.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen P E et al (1993) Anticancer Drug Des 8:53–63).

A "variant" of H-nm23 is defined as an amino acid sequence that is different by one or more amino acid substitutions. The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNASTAR software.

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to the naturally occurring H-nm23.

A "substitution" results from the replacement of one or more nucleotides or amino acids by different nucleotides or amino acids, respectively.

The term "biologically active" refers to a H-nm23 having structural, regulatory or biochemical functions of the naturally occurring H-nm23. Likewise, "immunologically active" defines the capability of the natural, recombinant or synthetic H-nm23, or any oligopeptide thereof, to induce a specific immune response in appropriate animals or cells and to bind with specific antibodies.

The term "derivative" as used herein refers to the chemical modification of a nucleic acid encoding H-nm23 or the encoded H-nm23. Illustrative of such modifications would be replacement of hydrogen by an alkyl, acyl, or amino group. A nucleic acid derivative would encode a polypeptide which retains essential biological characteristics of natural H-nm23.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated.

"Stringency" typically occurs in a range from about Tm-5° C. (5° C. below the Tm of the probe) to about 20° C. to 25° C. below Tm. As will be understood by those of skill in the art, a stringency hybridization can be used to identify or detect identical polynucleotide sequences or to identify or detect similar or related polynucleotide sequences.

The term "hybridization" as used herein shall include "any process by which a strand of nucleic acid joins with a complementary strand through base pairing" (Coombs J (1994) *Dictionary of Biotechnology*, Stockton Press, New York N.Y.). Amplification as carried out in the polymerase chain reaction technologies is described in Dieffenbach C W and G S Dveksler (1995, *PCR Primer, a Laboratory Manual*, Cold Spring Harbor Press, Plainview N.Y.).

Perferred Embodiment

The present invention relates to a novel human nm23-like protein, designated H-nm23, initially identified among the partial cDNAs from a human breast tissue library (BRSTNOT05) and to the use of the nucleic acid and amino acid sequences disclosed herein in the study, diagnosis, prevention and treatment of disease. Northern analysis using the LIFESEQ™ database (Incyte Pharmaceuticals, Palo Alto Calif.) shows that mRNA encoding H-nm23 was found in tissues isolated from small intestine, prostate, ovary, lymph node, breast spinal cord, thyroid, colon, lung and bladder tissues (FIG. 4). Of the 41 cDNA libraries containing H-nm23 mRNA, ten were derived from prostate tissue. Five of these libraries were from prostate tumors. Of the five non-tumor prostate libraries, four were generated from non-cancerous tissues excised from cancer patients, and the remaining library was derived from a young man asymptomatic of cancer. H-nm23 mRNA was also found in fetal and neonatal heart, spleen, lung, and kidney, but was not found in these organs in adults, indicating that H-nm23 may be related to the development of these tissues. The single exception to this trend was the presence of H-nm23 in adult heart myoma (atrial myxoma), a benign tumor. H-nm23 mRNA was also transcribed in the hNT2 cell line, which was derived from a human teratocarcinoma that exhibited properties characteristic of a committed neuronal precursor at an early stage of development.

The present invention also encompasses H-nm23 variants. A preferred H-nm23 variant is one having at least 80% amino acid sequence similarity to the H-nm23 amino acid sequence (SEQ ID NO:1), a more preferred H-nm23 variant is one having at least 90% amino acid sequence similarity to SEQ ID NO:1 and a most preferred H-nm23 variant is one having at least 95% amino acid sequence similarity to SEQ ID NO:1.

The nucleic acid sequence encoding a portion of H-nm23 was first identified in the cDNA, Incyte Clone 964996, through a computer-generated search for amino acid sequence alignments. The nucleic acid sequence, SEQ ID NO:2, disclosed herein (FIGS. 1A, 1B and 1C) encodes the amino acid sequence, SEQ ID NO:1, designated H-nm23. The full length cDNA was assembled from Incyte Clones 603550 (BRSTTUT01); 668015 (SCORNOT01); 669792 (CRBLNOT01); 964996 (BRSTNOT05); 1211471 (BRSTNOT02); 1312720 (BLADTUT02); and 1403767 (LATRTUT02) from the LIFESEQ™ database (Incyte Pharmaceuticals, Palo Alto, Calif.).

Figure 2B:
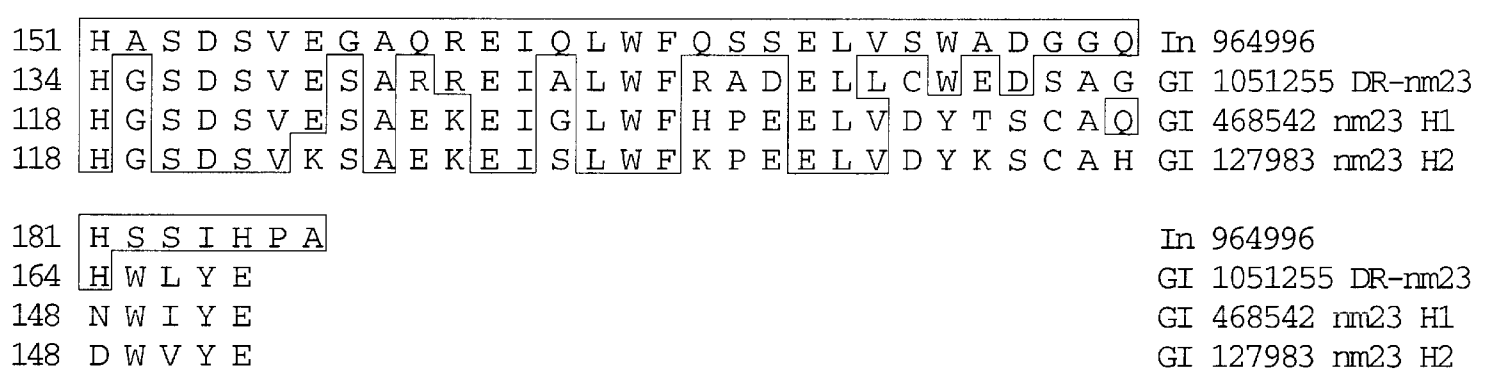

The present invention is based in part on the structural homology shown in FIGS. 2A and 2B, among H-nm23 and other human nm23 isoforms including DR-nm23 (GI 1051256; Venturelli D et al, supra), nm23-H1 (GI 468542, Rosengard A M et al, supra) and nm23-H2 (GI 127983, Stahl J A et al, supra). DR-nm23, nm23-H1, and nm23-H2 have, respectively, 50%, 46% and 44% amino acid sequence identity to H-nm23.

The H-nm23 protein sequence consists of 187 amino acids. From positions 68 to 97 the amino acid sequence contains a periodic repetition of leucine residues at every sixth to seventh position. This pattern is characteristic of a leucine zipper motif, which is present in many gene regulatory proteins (Busch S J et al (1990) Trends Genet 6:36–40). H-nm23 has an arg-gly-asp sequence at positions 138–140. This sequence, known as the "RGD motif", is crucial in the interaction of fibronectin with its integrin cell-surface receptor, and plays a role in cell adhesion (d'Souza S E et al (1991) Trends Biochem Sci 16:246–250). H-nm23 also contains the consensus sequence for NDPK (Gilles A M et al, supra) which includes the active site histidine at position 151.

THE H-nm23 CODING SEQUENCES

The nucleic acid and amino acid sequences of H-nm23 are shown in FIGS. 1A, 1B and 1C. In accordance with the invention, any nucleic acid sequence which encodes the amino acid sequence of H-nm23 can be used to generate recombinant molecules which express H-nm23. In a specific embodiment described herein, a partial sequence of H-nm23 was first isolated as Incyte Clone 964996 from a human breast tissue library (BRSTNOT05).

It will be appreciated by those skilled in the art that as a result of the degeneracy of the genetic code, a multitude of nucleotide sequences encoding H-nm23, some bearing minimal homology to the nucleotide sequences of any known and naturally occurring gene, may be produced. The invention contemplates each and every possible variation of nucleotide sequence that could be made by selecting combinations based on possible codon choices. These combinations are made in accordance with the standard triplet genetic code as applied to the nucleotide sequence of naturally occurring H-nm23, and all such variations are to be considered as being specifically disclosed.

Although nucleotide sequences which encode H-nm23 and its variants are preferably capable of hybridizing to the nucleotide sequence of the naturally occurring H-nm23 under appropriately selected conditions of stringency, it may be advantageous to produce nucleotide sequences encoding H-nm23 or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding H-nm23 and its derivatives without altering the encoded amino acid sequences include the production of RNA transcripts having more desirable properties, such as a greater half-life, than transcripts produced from the naturally occurring sequence.

It is now possible to produce a DNA sequence, or portions thereof, encoding a H-nm23 and its derivatives entirely by synthetic chemistry, after which the synthetic gene may be inserted into any of the many available DNA vectors and cell systems using reagents that are well known in the art at the time of the filing of this application.

Moreover, synthetic chemistry may be used to introduce mutations into a gene encoding H-nm23.

Also included within the scope of the present invention are polynucleotide sequences that are capable of hybridizing to the nucleotide sequence of FIGS. 1A and 1B and 1C under various conditions of stringency. Hybridization conditions are based on the melting temperature (Tm) of the nucleic acid binding complex or probe, as taught in Berger and Kimmel (1987, *Guide to Molecular Cloning Techniques, Methods in Enzymology*, Vol 152, Academic Press, San Diego Calif.) incorporated herein by reference, and confer may be used at a defined stringency.

Altered nucleic acid sequences encoding H-nm23 which may be used in accordance with the invention include deletions, insertions or substitutions of different nucleotides resulting in a polynucleotide that encodes the same or a functionally equivalent H-nm23. The protein may also show deletions, insertions or substitutions of amino acid residues which produce a silent change and result in a functionally equivalent H-nm23. Deliberate amino acid substitutions may be made on the basis of similarity in polarity, charge, solubility, hydrophobicity, hydrophilicity, and/or the amphipathic nature of the residues as long as the biological activity of H-nm23 is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles of H-nm23. As used herein, an "allele" or "allelic sequence" is an alternative form of H-nm23. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

Methods for DNA sequencing are well known in the art and employ such enzymes as the Klenow fragment of DNA polymerase I, SEQUENASE (US Biochemical Corp, Cleveland Ohio), Taq polymerase (Perkin Elmer, Norwalk Conn.), thermostable T7 polymerase (Amersham, Chicago Ill.), or combinations of recombinant polymerases and proofreading exonucleases such as the ELONGASE Amplification System marketed by Gibco BRL (Gaithersburg Md.). Preferably, the process is automated with machines such as the Hamilton Micro Lab 2200 (Hamilton, Reno Nev.), Peltier Thermal Cycler (PTC200; M J Research, Watertown Mass.) and the ABI 377 DNA sequencers (Perkin Elmer).

Extending the Polynucleotide Sequence

The polynucleotide sequence encoding H-nm23 may be extended utilizing partial nucleotide sequence and various methods known in the art to detect upstream sequences such as promoters and regulatory elements. Gobinda et al (1993; PCR Methods Applic 2:318–22) disclose "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al (1988) Nucleic Acids Res 16:8186). The primers may be designed using OLIGO® 4.06 Primer Analysis Software (1992; National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Another method which may be used to retrieve unknown sequences is that of Parker J D et al (1991; Nucleic Acids Res 19:3055–60). Additionally, one can use PCR, nested primers and PROMOTERFINDER libraries to walk in genomic DNA (PROMOTERFINDER Clontech (Palo Alto Calif.). This process avoids the need to screen libraries and is useful in finding intron/exon junctions.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

Capillary electrophoresis may be used to analyze the size or confirm the nucleotide sequence of sequencing or PCR products. Systems for rapid sequencing are available from Perkin Elmer, Beckman Instruments (Fullerton Calif.), and other companies. Capillary sequencing may employ flowable polymers for electrophoretic separation, four different fluorescent dyes (one for each nucleotide) which are laser activated, and detection of the emitted wavelengths by a charge coupled device camera. Output/light intensity is converted to electrical signal using appropriate software (eg. GENOTYPER and SEQUENCE NAVIGATOR from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez M C et al (1993) Anal Chem 65:2851–8).

Expression of the Nucleotide Sequence

In accordance with the present invention, polynucleotide sequences which encode H-nm23, fragments of the polypeptide, fusion proteins or functional equivalents thereof may be used in recombinant DNA molecules that direct the expression of H-nm23 in appropriate host cells. Due to the inherent degeneracy of the genetic code, other DNA sequences which encode substantially the same or a functionally equivalent amino acid sequence, may be used to clone and express H-nm23. As will be understood by those of skill in the art, it may be advantageous to produce H-nm23-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of H-nm23 expression or to produce recombinant RNA transcripts having desirable properties, such as a longer half-life, than transcripts produced from naturally occurring sequence.

The nucleotide sequences of the present invention can be engineered in order to alter a coding sequence of H-nm23 for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, to produce splice variants, etc.

In another embodiment of the invention, a natural, modified or recombinant nucleotide sequence encoding H-nm23 may be ligated to a heterologous sequence to encode a fusion protein. For example, for screening of peptide libraries for inhibitors of H-nm23 activity, it may be useful to encode a chimeric H-nm23 protein that is recognized by a commercially available antibody. A fusion protein may also be engineered to contain a cleavage site located between a H-nm23 sequence and the heterologous protein sequence, so that the H-nm23 may be cleaved and substantially purified away from the heterologous moiety.

In an alternate embodiment of the invention, the coding sequence for H-nm23 may be synthesized, whole or in part, using chemical methods well known in the art (see Caruthers M H et al (1980) Nuc Acids Res Symp Ser 215–23, Horn T et al(1980) Nuc Acids Res Symp Ser 225–32, etc). Alternatively, the protein itself could be produced using chemical methods to synthesize a H-nm23 amino acid sequence, whole or in part. For example, peptide synthesis can be performed using various solid-phase techniques (Roberge J Y et al (1995) Science 269:202–204) and automated synthesis may be achieved, for example, using the ABI 431A Peptide Synthesizer (Perkin Elmer) in accordance with the instructions provided by the manufacturer.

The newly synthesized peptide can be substantially purified by preparative high performance liquid chromatography (eg, Creighton (1983) *Proteins, Structures and Molecular Principles*, W H Freeman and Co, New York N.Y.). The composition of the synthetic peptides may be confirmed by amino acid analysis or sequencing (eg, the Edman degradation procedure; Creighton, supra). Additionally the amino acid sequence of H-nm23, or any part thereof, may be altered during direct synthesis and/or combined using chemical methods with sequences from other proteins, or any part thereof, to produce a variant polypeptide.

Expression Systems

In order to express a biologically active H-nm23, the nucleotide sequence encoding H-nm23 or its functional equivalent, is inserted into an appropriate expression vector, ie, a vector which contains the necessary elements for the transcription and translation of the inserted coding sequence.

Methods which are well known to those skilled in the art can be used to construct expression vectors containing a H-nm23 coding sequence and appropriate transcriptional or translational controls. These methods include in vitro recombinant DNA techniques, synthetic techniques and in vivo recombination or genetic recombination. Such techniques are described in Sambrook et al (1989) *Molecular Cloning, a Laboratory Manual*, Cold Spring Harbor Press, Plainview N.Y. and Ausubel F M et al (1989). *Current Protocols in Molecular Biology*, John Wiley & Sons, New York N.Y.

A variety of expression vector/host systems may be utilized to contain and express a H-nm23 coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, La Jólla Calif.) or PSPORT1 (Gibco BRL) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of H-nm23, vectors based on SV40 or EBV may be used with an appropriate selectable marker.

In bacterial systems, a number of expression vectors may be selected depending upon the use intended for H-nm23. For example, when large quantities of H-nm23 are needed for the induction of antibodies, vectors which direct high level expression of fusion proteins that are readily purified may be desirable. Such vectors include, but are not limited to, the multifunctional *E. coli* cloning and expression vectors such as BLUESCRIPT (Stratagene), in which the H-nm23 coding sequence may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase and PGH may be used. For reviews, see Ausubel et al (supra) and Grant et al (1987) Methods in Enzymology 153:516–544.

In cases where plant expression vectors are used, the expression of a sequence encoding H-nm23 may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J and Sinibaldi R M (1991) Results Probl Cell Differ 17:85–105) may be used. These constructs can be introduced into plant cells by direct DNA transformation or pathogen-mediated transfection. For reviews of such techniques, see Hobbs S or Murry L E in McGraw Hill *Yearbook of Science and Technology* (1992) McGraw Hill New York N.Y., pp 191–196 or Weissbach and Weissbach (1988) *Methods for Plant Molecular Biology*, Academic Press, New York N.Y., pp 421–463.

An alternative expression system which could be used to express H-nm23 is an insect system. In one such system, *Autographa californica* nuclear polyhedrosis virus (AcNPV) is used as a vector to express foreign genes in *Spodoptera frugiperda* cells or in Trichoplusia larvae. The H-nm23 coding sequence may be cloned into a nonessential region of the virus, such as the polyhedrin gene, and placed under control of the polyhedrin promoter. Successful insertion of the H-nm23 coding sequence will render the polyhedrin gene inactive and produce recombinant virus lacking coat protein coat. The recombinant viruses are then used to infect *S. frugiperda* cells or Trichoplusia larvae in which H-nm23 is expressed (Smith et al (1983) J Virol 46:584; Engelhard E K et al (1994) Proc Nat Acad Sci 91:3224–7).

In mammalian host cells, a number of viral-based expression systems may be utilized. In cases where an adenovirus is used as an expression vector, a coding sequence for H-nm23 may be ligated into an adenovirus transcription/translation complex consisting of the late promoter and tripartite leader sequence. Insertion in a nonessential E1 or E3 region of the viral genome will result in a viable virus capable of expressing H-nm23 in infected host cells (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of a H-nm23 sequence. These signals include the ATG initiation codon and adjacent sequences. In cases where nucleic acid encoding H-nm23, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express H-nm23 may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M et al (1977) Cell 11:223–32) and adenine phosphoribosyltransferase (Lowy I et al (1980) Cell 22:817–23) genes which can be employed in tk- or aprt-cells, respectively. Also, antimetabolite, antibiotic or herbicide resistance can be used as the basis for selection; for example, dhfr which confers resistance to methotrexate (Wigler M et al (1980) Proc Natl Acad Sci 77:3567–70); npt, which confers resistance to the aminoglycosides neomycin and G-418 (Colbere-Garapin F et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S C and R C Mulligan (1988) Proc Natl Acad Sci 85:8047–51). Recently, the use of visible markers has gained popularity with such markers as anthocyanins, a glucuronidase and its substrate, GUS, and luciferase and its substrate, luciferin, being widely used not only to identify transformants, but also to quantify the amount of transient or stable protein expression attributable to a specific vector system (Rhodes C A et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the H-nm23 polynucleotide sequence is inserted within a marker gene sequence, recombinant cells containing H-nm23 can be identified by the absence of marker gene function. Alternatively, a marker gene can be placed in tandem with a H-nm23 sequence under the control of a single promoter. Expression of the marker gene in response to induction or selection usually indicates expression of the tandem H-nm23 as well.

Alternatively, host cells which contain the coding sequence for H-nm23 and express H-nm23 may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the polynucleotide sequence encoding H-nm23 can be detected by DNA-DNA or DNA-RNA hybridization or amplification using probes, portions or fragments of H-nm23-encoding nucleotides. Nucleic acid amplification based assays involve the use of oligonucleotides or oligomers based on the H-nm23 sequence to detect transformants containing H-nm23 DNA or RNA. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of H-nm23, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on H-nm23 is preferred, but a competitive binding assay may be employed. These and other assays are described, among other places, in Hampton R et al (1990, *Serological Methods, a Laboratory Manual*, APS Press, St Paul Minn.) and Maddox D E et al (1983, J Exp Med 158:1211).

A wide variety of labels and conjugation techniques are known by those skilled in the art and can be used in various nucleic acid and amino acid assays. Means for producing labeled hybridization or PCR. probes for detecting sequences related to H-nm23 include oligolabeling, nick translation, end-labeling or PCR amplification using a labeled nucleotide. Alternatively, the H-nm23 sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 incorporated herein by reference.

Purification of H-nm23

Host cells transformed with a H-nm23-encoding nucleotide sequence may be cultured under conditions suitable for the expression and recovery of the encoded protein from cell culture. The protein produced by a recombinant cell may be contained intracellularly or secreted depending on the sequence and/or the vector used. As will be understood by those of skill in the art, expression vectors containing H-nm23 can be designed for efficient production and proper transmembrane insertion of H-nm23 into a prokaryotic or eukaryotic cell membrane. Other recombinant constructions may join H-nm23 to nucleotide sequence encoding a polypeptide domain which will facilitate purification of soluble proteins (Kroll D J et al (1993) DNA Cell Biol 12:441–53; cf discussion of vectors infra containing fusion proteins).

H-nm23 may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor XA or enterokinase (Invitrogen, San Diego Calif.) between the purification domain and H-nm23 is useful to facilitate purification. One such expression vector provides for expression of a fusion protein compromising an H-nm23 and contains nucleic acid encoding 6 histidine residues followed by thioredoxin and an enterokinase cleavage site. The histidine residues facilitate purification on IMIAC (immobilized metal ion affinity chromatography as described in Porath et al (1992) Protein Expression and Purification 3: 263–281) while the enterokinase cleavage site provides a means for purifying the H-nm23 from the fusion protein.

In addition to recombinant production, fragments of H-nm23 may be produced by direct peptide synthesis using solid-phase techniques (cf Stewart et al (1969) Solid-Phase Peptide Synthesis, W H Freeman Co, San Francisco; Merrifield J (1963) J Am Chem Soc 85:2149–2154). In vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments of H-nm23 may be chemically synthesized separately and combined using chemical methods to produce the full length molecule.

Uses of H-nm23

The rationale for the use of polynucleotide and polypeptide sequences disclosed herein is based in part on the chemical and structural homology among the novel H-nm23 and human isoforms of nm23. H-nm23 may be used in the diagnosis, prognosis and treatment of diseases associated with abnormal tissue development and differentiation including cancer.

H-nm23 may be useful as a tumor suppressor or a metastatic inhibitor, decreasing the severity or the metastatic potential of certain tumor types.

A correlation between expression of H-nm23 and metastasis in specific tumors would provide a measure of metastatic potential. In such tumor types, H-nm23 may be useful as a prognostic marker. Antibodies specifically recognizing H-nm23 may be used to quantitate H-nm23 for prognostic and diagnostic purposes.

H-nm23 or its fragments can be used to identify specific molecules with which it interacts. Such molecules include agonists that enhance H-nm23 activity. Furthermore, DNA segments to which H-nm23 binds may reveal promoter regions or other regulatory sites important in the control of cell cycle or tumor-associated genes.

H-nm23 Antibodies

H-nm23-specific antibodies are useful for the diagnosis and prognosis of conditions and diseases associated with expression of H-nm23. Such antibodies may include, but are not limited to, polyclonal, monoclonal, chimeric, single chain, Fab fragments and fragments produced by a Fab expression library. Neutralizing antibodies, ie, those which inhibit dimer formation, are especially preferred for diagnostics and therapeutics.

H-nm23 for antibody induction does not require biological activity; however, the protein fragment, or oligopeptide must be antigenic. Peptides used to induce specific antibodies may have an amino acid sequence consisting of at least five amino acids, preferably at least 10 amino acids. Preferably, they should mimic a portion of the amino acid sequence of the natural protein and may contain the entire amino acid sequence of a small, naturally occurring molecule. Short stretches of H-nm23 amino acids may be fused with those of another protein such as keyhole limpet hemocyanin and antibody produced against the chimeric molecule. Procedures well known in the art can be used for the production of antibodies to H-nm23.

For the production of antibodies, various hosts including goats, rabbits, rats, mice, etc may be immunized by injection with H-nm23 or any portion, fragment or oligopeptide which retains immunogenic properties. Depending on the host species, various adjuvants may be used to increase immunological response. Such adjuvants include but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium paryum* are potentially useful human adjuvants.

Monoclonal antibodies to H-nm23 may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy*, Alan R Liss Inc, New York N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce H-nm23-specific single chain antibodies Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for H-nm23 may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse W D et al (1989) Science 256:1275–1281).

A variety of protocols for competitive binding or immunoradiometric assays using either polyclonal or monoclonal antibodies with established specificities are well known in the art. Such immunoassays typically involve the formation of complexes between H-nm23 and its specific antibody and the measurement of complex formation. A two-site, monoclonal-based immunoassay utilizing monoclonal antibodies reactive to two noninterfering epitopes on a specific H-nm23 protein is preferred, but a competitive binding assay may also be employed. These assays are described in Maddox D E et al (1983, J Exp Med 158:1211).

Diagnostic Assays Using H-nm3 Specific Antibodies

Particular H-nm23 antibodies are useful for the diagnosis of conditions or diseases characterized by expression of H-nm23 or in assays to monitor patients being treated with H-nm23, agonists or inhibitors. Diagnostic assays for H-nm23 include methods utilizing the antibody and a label to detect H-nm23 in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring H-nm23, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on H-nm23 is preferred, but a competitive binding assay may be employed. These assays are described, among other places, in Maddox, D E et al (1983, J Exp Med 158:1211).

In order to provide a basis for diagnosis, normal or standard values for H-nm23 expression must be established. This is accomplished by combining body fluids or cell extracts taken from normal subjects, either animal or human, with antibody to H-nm23 under conditions suitable for complex formation which are well known in the art. The amount of standard complex formation may be quantified by comparing various artificial membranes containing known quantities of H-nm23 with both control and disease samples from biopsied tissues. Then, standard values obtained from normal samples may be compared with values obtained from samples from subjects potentially affected by disease. Deviation between standard and subject values establishes the presence of disease state.

Drug Screening

H-nm23, its catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellularly. The formation of binding complexes, between H-nm23 and the agent being tested, may be measured.

Another technique for drug screening which may be used for high throughput screening of compounds having suitable binding affinity to the H-nm23 is described in detail in "Determination of Amino Acid Sequence Antigenicity" by Geysen H M, WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of H-nm23 and washed. Bound H-nm23 is then detected by methods well known in the art. Substantially purified H-nm23 can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding H-nm23 specifically compete with a test compound for binding H-nm23. In this manner, the antibodies can be used to detect the presence of any peptide which shares one or more antigenic determinants with H-nm23.

Uses of the Polynucleotide Encoding H-nm23

A polynucleotide encoding H-nm23, or any part thereof, may be used for diagnostic and/or therapeutic purposes. For diagnostic purposes, the H-nm23 of this invention may be used to detect and quantitate gene expression in biopsied tissues in which expression of H-nm23 may be implicated. The diagnostic assay is useful to distinguish between absence, presence, and excess expression of H-nm23 and to monitor regulation of H-nm23 levels during therapeutic intervention. Included in the scope of the invention are oligonucleotide sequences, antisense RNA and DNA molecules, and PNAs.

Another aspect of the subject invention is to provide for hybridization or PCR probes which are capable of detecting polynucleotide sequences, including genomic sequences, encoding H-nm23 or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or low) will determine whether the probe identifies only naturally occurring H-nm23, alleles or related sequences.

Probes may also be used for the detection of related sequences and should preferably contain at least 50% of the nucleotides from any of these H-nm23 encoding sequences. The hybridization probes of the subject invention may be derived from the nucleotide sequence of SEQ ID NO:2 or from genomic sequence including promoter, enhancer elements and introns of the naturally occurring H-nm23. Hybridization probes may be labeled by a variety of reporter groups, including radionuclides such as $^{12}p$ or $^{35}S$, or enzymatic labels such as alkaline phosphatase coupled to the probe via avidin/biotin coupling systems, and the like.

Other means for producing specific hybridization probes for H-nm23 DNAs include .he cloning of nucleic acid sequences encoding H-nm23 or H-nm23 derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

Diagnostic Use

Polynucleotide sequences encoding H-nm23 may be used for the diagnosis of conditions or diseases with which the expression of H-nm23 is associated. For example, polynucleotide sequences encoding H-nm23 may be used in hybridization or PCR assays of fluids or tissues from biopsies to detect H-nm23 expression. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits.

The H-nm23 nucleotide sequence disclosed herein provide the basis for assays that detect activation or induction associated with disease. The H-nm23 nucleotide sequence may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of H-nm23 nucleotide sequences in the sample indicates the presence of the associated inflammation and/or disease.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for H-nm23 expression must be established. This is accomplished by combining body fluids or cell extracts taken from normal subjects, either animal or human, with H-nm23, or a portion thereof, under conditions suitable for hybridization or amplification. Standard hybridization may be quantified by comparing the values obtained for normal subjects with a dilution series of H-nm23 run in the same experiment where a known amount of substantially purified H-nm23 is used. Standard values obtained from normal samples may be compared with values obtained from samples from patients afflicted with H-nm23-associated diseases. Deviation between standard and subject values is used to establish the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

Polymerase Chain Reaction (PCR) as described in U.S. Pat. Nos. 4,683,195 and 4,965,188 provides additional uses for oligonucleotides based upon the H-nm23 sequence. Such oligomers are generally chemically synthesized, but they may be generated enzymatically or produced from a recombinant source. Oligomers generally comprise two nucleotide sequences, one with sense orientation (5'–>3') and one with antisense (3'<–5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods which may be used to quantitate the expression of a particular molecule include radiolabeling (Melby P C et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. A definitive diagnosis of this type may allow health professionals to begin aggressive treatment and prevent further worsening of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Therapeutic Use

Based upon its homology to the genes encoding the nm23 isoforms and its expression profile, the H-nm23 polynucleotide disclosed herein may provide the basis for the design of molecules for the treatment of cancer or other disorders associated with abnormal tissue development or differentiation.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antisense H-nm23. See, for example, the techniques described in Sambrook et al (supra) and Ausubel et al (supra).

The polynucleotides comprising full length cDNA sequence and/or its regulatory elements enable researchers to use H-nm23 as an investigative tool in sense (Youssoufian H and H F Lodish 1993 Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding H-nm23 can be turned off by transfecting a cell or tissue with expression vectors which express high levels of a desired H-nm23 fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler I, personal communication) and even longer if appropriate replication elements are part of the vector system.

As mentioned above, modifications of gene expression can be obtained by designing antisense molecules, DNA, RNA or PNA, to the control regions of H-nm23, ie, the promoters, enhancers, and introns. Oligonucleotides derived from the transcription initiation site, eg, between –10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J E et al (In: Huber B E and B I Carr (1994) *Molecular and Immunologic Approaches*, Futura Publishing Co, Mt Kisco N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of RNA encoding H-nm23.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by n vitro and n vivo transcription of DNA sequences encoding H-nm23. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2'O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient is presented in U.S. Pat. Nos. 5,399,493 and 5,437,994, disclosed herein by reference. Delivery by transfection and by liposome are quite well known in the art.

Furthermore, the nucleotide sequences for H-nm23 disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence for H-nm23 can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price C M (1993; Blood Rev 7:127–34) and Trask B J (1991; Trends Genet 7:149–54).

The technique of fluorescent in situ hybridization of chromosome spreads has been described, among other places, in Verma et al (1988) *Human Chromosomes: A Manual of Basic Techniques*, Pergamon Press, New York N.Y. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a H-nm23 on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

In situ hybridization of chromosomal preparations and physical mapping techniques such as linkage analysis using established chromosomal markers may be used for extending genetic maps. For example, an STS based map of the human genome was recently published by the Whitehead-MIT Center for Genomic Research (Hudson T J et al (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention relates to pharmaceutical compositions which may comprise nucleotides, proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition. For administration of H-nm23, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combinations), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for nucleotides than for proteins or their inhibitors. Similarly, delivery of polynucleotides or polypeptides will be specific to particular cells, conditions, locations, etc.

The examples below are provided to illustrate the subject invention and are not included for the purpose of limiting the invention.

EXAMPLES

I cDNA Library Construction

The normal breast (BRSTNOT05) and breast carcinoma (BRSTTUT03) cDNA libraries were constructed from the breast tissue of a 58 year old Caucasian female. The patient was diagnosed with multicentric invasive grade 4 lobular carcinoma. The normal breast tissue is adjacent, microscopically normal tissue.

The frozen tissue was homogenized and lysed using a Brinkmann Homogenizer Polytron PT-3000 (Brinkmann Instruments, Westbury N.J.) in guanidinium isothiocyanate solution. The lysate was centrifuged over a 5.7 M CsCl cushion using an Beckman SW28 rotor in a Beckman L8-70M Ultracentrifuge (Beckman Instruments) for 18 hours at 25,000 rpm at ambient temperature. The RNA was extracted with acid phenol pH 4.0, precipitated using 0.3 M sodium acetate and 2.5 volumes of ethanol, resuspended in RNAse-free water and DNase treated at 37° C. The RNA extraction was repeated with acid phenol chloroform pH 8.0 and precipitated with sodium acetate and ethanol as before. The mRNA was then isolated using the Qiagen Oligotex kit (QIAGEN Inc; Chatsworth Calif.) and used to construct the cDNA library.

The mRNA was handled according to the recommended protocols in the SuperScript Plasmid System for cDNA Synthesis and Plasmid Cloning (Cat. #18248–013; Gibco/BRL), cDNAs were fractionated on a Sepharose CL4B column (Cat. #275105–01; Pharmacia), and those cDNAs exceeding 400 bp were ligated into PSPORT I. The plasmid pSport I was subsequently transformed into DH5A competent cells (Cat. #18258–012; Gibco/BRL).

II Isolation and Sequencing of cDNA Clones

Plasmid DNA was released from the cells and purified using the REAL Prep 96 Plasmid Kit for Rapid Extraction Alkaline Lysis Plasmid Minipreps (Catalog #26173; QIAGEN, Inc). This kit enables the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, LIFE TECHNOLOGIES™) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 40 C.

The cDNAs were sequenced by the method of Sanger F and A R Coulson (1975; J Mol Biol 94:441f), using a Hamilton Micro Lab 2200 (Hamilton, Reno Nev.) in combination with Peltier Thermal Cyclers (PTC200 from M J Research, Watertown Mass.) and Applied Biosystems 377 DNA Sequencing Systems; and the reading frame was determined.

III Homology Searching of cDNA Clones and Their Deduced Proteins

Each cDNA was compared to sequences in GenBank using a search algorithm developed by Applied Biosystems and incorporated into the INHERIT 670 Sequence Analysis System. In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul S F (1993) J Mol Evol 36:290–300; Altschul, S F et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al. supra).

Analogous computer techniques use BLAST (Altschul S F 1993 and 1990, supra) to search for identical or related molecules in nucleotide databases such as GenBank or the LIFESEQ™ database (Incyte, Palo Alto Calif.). This analysis is much faster than multiple, membrane-based hybridizations. In addition, the sensitivity of the computer search can be modified to determine whether any particular match is categorized as exact or homologous.

The basis of the search is the product score which is defined as:

$$\% \text{ sequence identity} \times \% \text{ maximum BLAST score}/100$$

and it takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of the search are reported as a list of libraries in which the full length sequence, or parts thereof, is represented, the abundance of the sequence, and the percent abundance. Abundance directly reflects the number of times a particular transcript is present in a cDNA library, and percent abundance is abundance divided by the total number of sequences examined in the library.

Extension of H-nm23 to Full Length or to Recover Regulatory Elements

The nucleic acid sequence encoding full length H-nm23 (SEQ ID NO:2) is used to design oligonucleotide primers for extending a partial nucleotide sequence to full length or for obtaining 5' sequences from genomic libraries. One primer is synthesized to initiate extension in the antisense direction (XLR) and the other is synthesized to extend sequence in the sense direction (XLF). Primers allow the extension of the known H-nm23 nucleotide sequence "outward" generating amplicons containing new, unknown nucleotide sequence for the region of interest (U.S. patent application Ser. No. 08/487,112, filed Jun. 7, 1995, specifically incorporated by reference). The initial primers are designed from the cDNA using OLIGO® 4.06 Primer Analysis Software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M J Research, Watertown Mass.) and the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat step 4–6 for 15 additional cycles
Step 8 94° C. for 15 sec
Step 9 65° C. for 1 min
Step 10 68° C. for 7:15 min
Step 11 Repeat step 8–10 for 12 cycles
Step 12 72° C. for 8 min
Step 13 4° C. (and holding)

A 5–10 µl aliquot of the reaction mixture is analyzed by electrophoresis on a low concentration (about 0.6–0.8%) agarose mini-gel to determine which reactions were successful in extending the sequence. Bands thought to contain the largest products were selected and cut out of the gel. Further purification involves using a commercial gel extraction method such as QIAQUICK (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent *E. coli* cells (in 40 µl of appropriate media) are transformed with 3 µl of ligation mixture and cultured m 80 µA of SOC medium (Sambrook J et al, supra). After incubation for one hour at 37° C. transformation mixture is plated on Luria Bertani (LB)-agar (Sambrook J et al, supra) containing 2×Carb. The following day, several colonies are randomly picked from each plate and cultured in 150 µl of liquid LB/2×Carb medium placed in an individual well of an appropriate, commercially-available, sterile 96-well plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3×) containing 4 units of rTth DNA polymerase, a vector primer and one or both of the gene specific primers used for the extension reaction are added to each well. Amplification is performed using the following conditions:

Step 1 94° C. for 60 sec
Step 2 94° C. for 20 sec
Step 3 55° C. for 30 sec
Step 4 72° C. for 90 sec
Step 5 Repeat steps 2–4 for an additional 29 cycles
Step 6 72° C. for 180 sec
Step 7 4° C. (and holding)

Aliquots of the PCR reactions are run on agarose gels together with molecular weight markers. The sizes of the PCR products are compared to the original partial cDNAs, and appropriate clones are selected, ligated into plasmid and sequenced.

VI Labeling and Use of Hybridization Probes

Hybridization probes derived from SEQ ID NO:2 are employed to screen cDNAs, genomic DNAs or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 mCi of [$\gamma$-$^{32}$P] adenosine triphosphate (Amersham, Chicago Ill.) and T4 polynucleotide kinase (DuPont NEN®, Boston Mass.). The labeled oligonucleotides are substantially purified with Sephadex G-25 super fine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester N.Y.) is exposed to the blots or the blots are exposed in a PhosphorImager cassette (Molecular Dynamics, Sunnyvale Calif.) for several hours, hybridization patterns are compared visually.

VII Antisense Molecules

The nucleotide sequence encoding H-nm23, or any part thereof, is used to inhibit in vivo or in vitro expression of naturally occurring H-nm23. Although use of antisense oligonucleotides, comprising about 20 base-pairs, is specifically described, essentially the same procedure is used with larger cDNA fragments. An oligonucleotide based on the coding sequence of H-nm23 as shown in FIGS. 1A, 1B and 1C is used to inhibit expression of naturally occurring H-nm23. The complementary oligonucleotide is designed from the most unique 5' sequence as shown in FIGS. 1A, 1B and 1C and used either to inhibit transcription by preventing promoter binding to the upstream nontranslated sequence or translation of an H-nm23 transcript by preventing the ribosome from binding. Using an appropriate portion of the leader and 5' sequence of SEQ ID NO:2, an effective antisense oligonucleotide includes any 15–20 nucleotides spanning the region which translates into the signal or early coding sequence of the polypeptide as shown in FIGS. 1A, 1B and 1C.

VIII Expression of H-nm23

Expression of H-nm23 is accomplished by subcloning the cDNAs into appropriate vectors and transfecting the vectors into host cells. In this case, the cloning vector, PSPORT1, previously used for the generation of the cDNA library is used to express H-nm23 in *E. coli*. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length H-nm23. The signal sequence directs the secretion of H-nm23 into the bacterial growth media which can be used directly in the following assay for activity.

IX H-nm23 Activity

Binding of H-nm23 to DNA is assayed by monitoring the differences in electrophoretic mobility of the DNA with and without protein bound. A DNA probe (for example, a 105 base pair double-stranded fragment comprising the c-myc promoter region) is radiolabeled with $^{32}P$ by the transfer of the terminal phosphate of $[\gamma-^{32}P]ATP$ to the 5' ends of the DNA, catalyzed by T4 polynucleotide kinase (New England Biolabs, Beverly Mass.). The radiolabeled DNA is incubated with varying concentrations of H-nm23 at room temperature for approximately 1 hour. The incubation reactions are electrophoresed through non-denaturing polyacrylamide gels. The gels are dried and autoradiographed. The relative intensities of the bands corresponding to uncomplexed DNA and protein-complexed DNA for each concentration of added H-nm23 are determined by densitometry. The resulting titration curve is used along with the concentrations of the radiolabeled DNA and added H-nm23 to calculate values for the affinity of H-nm23 for the DNA.

The NDPK activity of H-nm23 is measured in a coupled pyruvate kinase-lactate dehydrogenase assay system (Sigma Chemical Co., St. Louis Mo.), with ATP as the phosphate donor and dTDP as the phosphate acceptor nucleotides. The ADP produced in the NDPK reaction reacts with phosphoenolpyruvate via the pyruvate kinase to form pyruvate. In the presence of pyruvate, the lactate dehydrogenase oxidizes NADH. NADH oxidation is accompanied by a change in absorbance at 340 nm, which is monitored in a spectrophotometer.

X Production of H-nm23 Specific Antibodies

H-nm23 substantially purified using PAGE electrophoresis (Sambrook, supra) is used to immunize rabbits and to produce antibodies using standard protocols. The amino acid sequence translated from H-nm23 is analyzed using DNASTAR software (DNAStar Inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions (shown in FIG. 3) is described by Ausubel F M et al (supra).

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel F M et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring H-nm23 Using Specific Antibodies

Naturally occurring or recombinant H-nm23 is substantially purified by immunoaffinity chromatography using antibodies specific for H-nm23. An immunoaffinity column is constructed by covalently coupling H-nm23 antibody to an activated chromatographic resin such as CnBr-activated Sepharose (Pharmacia Biotech). After the coupling, the resin is blocked and washed according to the manufacturer's instructions.

Cellular fractions from cells containing H-nm23 are prepared by solubilization of the whole cell and isolation of subcellular fractions by differential centrifugation, by the addition of detergent, or by other methods well known in the art. Alternatively, soluble H-nm23 containing a signal sequence may be secreted in useful quantity into the medium in which the cells are grown.

A fractionated H-nm23-containing preparation is passed over the immunoaffinity column, and the column is washed under conditions that allow the preferential absorbance of H-nm23 (eg, high ionic strength buffers in the presence of detergent). The column is eluted under conditions that disrupt antibody/H-nm23 binding (eg, a buffer of pH 2–3 or a high concentration of a chaotrope such as urea or thiocyanate ion), and H-nm23 is collected.

XII Identification of Molecules Which Interact with H-nm23

H-nm23 is useful as a research tools for identification, characterization and purification of molecules with which it interacts. In one embodiment of affinity purification, H-nm23 is covalently coupled to a chromatography column. Cells and their membranes are extracted, endogenous H-nm23 is removed and various H-nm23-free subcomponents are passed over the column. H-nm23-associated molecules bind to the column by virtue of their biological affinity. The H-nm23-complex is recovered from the column, dissociated and the recovered molecule is subjected to N-terminal protein sequencing, nucleic acid sequencing, or high-performance liquid chromatography/mass spectrometry (HPLC/MS), depending on the type of molecule. The amino acid or nucleotide sequence or mass spectral analysis is then used to identify the captured molecule or, in the case of a protein ligand, to design degenerate oligonucleotide probes for cloning its gene from an appropriate cDNA library.

In an alternate method, monoclonal antibodies are raised against H-nm23 and screened to identify those compounds which inhibit the binding of the antibody to H-nm23. These monoclonal antibodies may then used in affinity purification or expression cloning of associated molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

What is claimed is:

1. An isolated polypeptide selected from the group consisting of:
   a) a polypeptide comprising the amino acid sequence of SEQ ID NO:1,
   b) a polypeptide that is at least 90% identical to the amino acid sequence of SEQ ID NO:1, wherein said polypeptide has nucleoside diphosphate kinase (NDPK) activity, and
   c) an immunogenic fragment of the polypeptide consisting of the amino acid sequence of SEQ ID NO:1, wherein said fragment is at least 15 amino acid residues in length.

2. An isolated polypeptide of claim 1, comprising the amino acid sequence of SEQ ID NO:1.

3. A method for producing a polypeptide of claim 1 the method comprising:
   a) culturing a cell under conditions suitable for expression of the polypeptide, wherein said cell is transformed with a recombinant polynucleotide, and said recombinant polynucleotide comprises a promoter sequence operably linked to a polynucleotide encoding the polypeptide of claim 1, and
   b) recovering the polypeptide so expressed.

4. A composition comprising a polypeptide of claim 1 and an excipient.

5. A composition of claim 4, wherein the polypeptide comprises the amino acid sequence of SEQ ID NO:1.

6. A method for screening a compound for effectiveness as an agonist of the nucleoside diphosphate kinase (NDPK) activity of a polypeptide selected from the group consisting of a polypeptide comprising the amino acid sequence of SEQ ID NO:1 and a polypeptide that is at least 90% identical to the amino acid sequence of SEQ ID NO:1, wherein said polypeptide has nucleoside diphosphate kinase (NDPK) activity, the method comprising:
   a) exposing a sample comprising said polypeptide to a compound, and
   b) detecting agonist activity in the sample.

7. A method for screening a compound for effectiveness as an antagonist of the nucleoside diphosphate kinase (NDPK) activity of a polypeptide selected from the group consisting of a polypeptide comprising the amino acid sequence of SEQ ID NO:1 and a polypeptide that is at least 90% identical to the amino acid sequence of SEQ ID NO:1, wherein said polypeptide has nucleoside diphosphate kinase (NDPK) activity the method comprising:
   a) exposing a sample comprising said polypeptide to a compound, and
   b) detecting antagonist activity in the sample.

8. A method of screening for a compound that specifically binds to a polypeptide of claim 1, said method comprising the steps of:
   a) combining the polypeptide of claim 1 with at least one test compound under suitable conditions, and
   b) detecting binding of the polypeptide of claim 1 to the test compound, thereby identifying a compound that specifically binds to the polypeptide of claim 1.

* * * * *

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
        (A) LENGTH: 187 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: <Unknown>
        (B) CLONE: Consensus (xi) SEQUENCE DESCRIPTION: SEQ ID NO: 1:

```
Met Gly Gly Leu Phe Trp Arg Ser Ala Leu Arg Gly Leu Arg Cys Gly
 1               5                  10                  15

Pro Arg Ala Pro Gly Pro Ser Leu Leu Val Arg His Gly Ser Gly Gly
            20                  25                  30

Pro Ser Trp Thr Arg Glu Arg Thr Leu Val Ala Val Lys Pro Asp Gly
        35                  40                  45

Val Gln Arg Arg Leu Val Gly Asp Val Ile Gln Arg Phe Glu Arg Arg
    50                  55                  60

Gly Phe Thr Leu Val Gly Met Lys Met Leu Gln Ala Pro Glu Ser Val
65                  70                  75                  80

Leu Ala Glu His Tyr Gln Asp Leu Arg Arg Lys Pro Phe Tyr Pro Ala
                85                  90                  95

Leu Ile Arg Tyr Met Ser Ser Gly Pro Val Val Ala Met Val Trp Glu
            100                 105                 110

Gly Tyr Asn Val Val Arg Ala Ser Arg Ala Met Ile Gly His Thr Asp
        115                 120                 125

Ser Ala Glu Ala Ala Pro Gly Thr Ile Arg Gly Asp Phe Ser Val His
    130                 135                 140

Ile Ser Arg Asn Val Ile His Ala Ser Asp Ser Val Glu Gly Ala Gln
145                 150                 155                 160

Arg Glu Ile Gln Leu Trp Phe Gln Ser Ser Glu Leu Val Ser Trp Ala
                165                 170                 175

Asp Gly Gly Gln His Ser Ser Ile His Pro Ala
            180                 185
```

(2) INFORMATION FOR SEQ ID NO: 2:

(i) SEQUENCE CHARACTERISTICS:
        (A) LENGTH: 986 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:

(A) LIBRARY: <Unknown>
    (B) CLONE: Consensus (xi) SEQUENCE DESCRIPTION: SEQ ID NO: 2:

```
GGCCGGGCGT CATGGGCGGC CTCTTCTGGC GCTCCGCGCT GCGGGGCTG  CGCTGCGGCC     60
CGCGGGCCCC GGGCCCGAGC CTGCTAGTGC GCCACGGCTC GGGAGGGCCC TCCTGGACCC    120
GGGAGCGGAC CCTGGTGGCG GTGAAGCCCG ATGGCGTGCA ACGGCGGCTC GTTGGGGACG    180
TGATCCAGCG CTTTGAGAGG CGGGGCTTCA CGCTGGTGGG GATGAAGATG CTGCAAGCAC    240
CAGAGAGCGT CCTTGCCGAG CACTACCAGG ACCTGCGGAG GAAGCCCTTC TACCCTGCCC    300
TMATCCGCTA CATGAGCTCT GGGCCTGTGG TGGCCATGGT CTGGGAAGGG TACAATGTCG    360
TCCGCGCCTC RAGGGCCATG ATTGGACACA CCGACTCGGC TGAGGCTGCC CCAGGAACCA    420
TAAGGGGTGA CTTCAGCGTC CACATCAGCA GGAATGTCAT CCACGCCAGC GACTCCGTGG    480
AGGGGGCCCA GCGGGAGATC CAGCTGTGGT TCCAGAGCAG TGAGCTGGTG AGCTGGGCAG    540
ACGGGGGCCA GCACAGCAGC ATCCACCCAG CCTGAGGCTC AAGCTGCCCT TACCACCCCA    600
TCCCCCACGC AGGACCAACT ACCTCCGTCA GCAAGAACCC AAGCCCACAT CCAAACCTGC    660
CTGTCCCAAA CCACTTACTT CCCTGTTCAC CTCTGCCCCA CCCCAGCCCA GAGGAGTTTG    720
AGCCACCAAC TTCAGTGCCT TTCTGTACCC CAAGCCAGCA CAAGATTGGA CCAATCCTTT    780
TTGCACCAAA GTGCCGGACA ACCTTTGTGG TGGGGGGGGG TCTTCACATT ATCATAACCT    840
CTCCTCTAAA GGGGAGGCAT TAAAATTCAC TGTGCCCAGC ACATGGGTGG TACACTAATT    900
ATGACTTCCC CCAGCTCTGA GGTAGAAATG ACGCCTTTAT GCAAGTTGTA AGGAGTTGAA    960
CAGTAAAGAG GAAGTTTTGC ACACCC                                        986
```

(2) INFORMATION FOR SEQ ID NO: 3:

(i) SEQUENCE CHARACTERISTICS:
        (A) LENGTH: 168 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 1051256

(xi) SEQUENCE DESCRIPTION: SEQ ID NO: 3:

```
Met Ile Cys Leu Val Leu Thr Ile Phe Ala Asn Leu Phe Pro Ala Ala
 1               5                  10                  15

Cys Thr Gly Ala His Glu Arg Thr Phe Leu Ala Val Lys Pro Asp Gly
             20                  25                  30

Val Gln Arg Arg Leu Val Gly Glu Ile Val Arg Arg Phe Glu Arg Lys
         35                  40                  45

Gly Phe Lys Leu Val Ala Leu Lys Leu Val Gln Ser Ser Glu Glu Leu
 50                  55                  60

Leu Arg Glu His Tyr Ala Glu Leu Arg Glu Arg Pro Phe Tyr Gly Arg
 65                  70                  75                  80

Leu Val Lys Tyr Met Ala Ser Gly Pro Val Val Ala Met Val Trp Gln
             85                  90                  95

Gly Leu Asp Val Val Arg Thr Ser Arg Ala Leu Ile Gly Ala Thr Asn
            100                 105                 110

Pro Ala Asp Ala Pro Pro Gly Thr Ile Arg Gly Asp Phe Cys Ile Glu
            115                 120                 125
```

Val Gly Asn Leu Ile His Gly Ser Asp Ser Val Glu Ser Ala Arg Arg
    130                 135                 140

Glu Ile Ala Leu Trp Phe Arg Ala Asp Glu Leu Leu Cys Trp Glu Asp
145                 150                 155                 160

Ser Ala Gly His Trp Leu Tyr Glu
                165

(2) INFORMATION FOR SEQ ID NO: 4:

(i) SEQUENCE CHARACTERISTICS:
        (A) LENGTH: 152 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 468542

(xi) SEQUENCE DESCRIPTION: SEQ ID NO: 4:

Met Ala Asn Cys Glu Arg Thr Phe Ile Ala Ile Lys Pro Asp Gly Val
1                 5                  10                  15

Gln Arg Gly Leu Val Gly Glu Ile Ile Lys Arg Phe Glu Gln Lys Gly
                20                  25                  30

Phe Arg Leu Val Gly Leu Lys Phe Met Gln Ala Ser Glu Asp Leu Leu
            35                  40                  45

Lys Glu His Tyr Val Asp Leu Lys Asp Arg Pro Phe Phe Ala Gly Leu
50                  55                  60

Val Lys Tyr Met His Ser Gly Pro Val Val Ala Met Val Trp Glu Gly
65                  70                  75                  80

Leu Asn Val Val Lys Thr Gly Arg Val Met Leu Gly Glu Thr Asn Pro
                85                  90                  95

Ala Asp Ser Lys Pro Gly Thr Ile Arg Gly Asp Phe Cys Ile Gln Val
            100                 105                 110

Gly Arg Asn Ile Ile His Gly Ser Asp Ser Val Glu Ser Ala Glu Lys
            115                 120                 125

Glu Ile Gly Leu Trp Phe His Pro Glu Glu Leu Val Asp Tyr Thr Ser
    130                 135                 140

Cys Ala Gln Asn Trp Ile Tyr Glu
145                 150

(2) INFORMATION FOR SEQ ID NO: 5:

(i) SEQUENCE CHARACTERISTICS:
        (A) LENGTH: 152 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 127983

(xi) SEQUENCE DESCRIPTION: SEQ ID NO: 5:

Met Ala Asn Leu Glu Arg Thr Phe Ile Ala Ile Lys Pro Asp Gly Val
1                 5                  10                  15

Gln Arg Gly Leu Val Gly Glu Ile Ile Lys Arg Phe Glu Gln Lys Gly
                20                  25                  30

-continued

```
Phe Arg Leu Val Ala Met Lys Phe Leu Arg Ala Ser Glu Glu His Leu
         35                  40                  45

Lys Gln His Tyr Ile Asp Leu Lys Asp Arg Pro Phe Phe Pro Gly Leu
     50                  55                  60

Val Lys Tyr Met Asn Ser Gly Pro Val Val Ala Met Val Trp Glu Gly
 65              70                  75                      80

Leu Asn Val Val Lys Thr Gly Arg Val Met Leu Gly Glu Thr Asn Pro
                 85                  90                  95

Ala Asp Ser Lys Pro Gly Thr Ile Arg Gly Asp Phe Cys Ile Gln Val
            100                 105                 110

Gly Arg Asn Ile Ile His Gly Ser Asp Ser Val Lys Ser Ala Glu Lys
        115                 120                 125

Glu Ile Ser Leu Trp Phe Lys Pro Glu Glu Leu Val Asp Tyr Lys Ser
    130                 135                 140

Cys Ala His Asp Trp Val Tyr Glu
145                 150
```